United States Patent
Landfield

(10) Patent No.: US 6,196,837 B1
(45) Date of Patent: Mar. 6, 2001

(54) PLIABLE MOUTHPIECE LARGE ANIMAL SPECULUM

(76) Inventor: Stacey Ann Landfield, 37559 Curces Dr., Warner Spr., CA (US) 92086

( * ) Notice: Subject to any disclaimer, the term of this patent is extended or adjusted under 35 U.S.C. 154(b) by 0 days.

(21) Appl. No.: 09/481,549

(22) Filed: Jan. 10, 2000

(51) Int. Cl.[7] .................................. A61D 5/00; A61B 1/32
(52) U.S. Cl. .............................. 433/1; 433/140; 600/238; 600/243
(58) Field of Search .................................. 600/235, 237, 600/238, 243, 244, 239; 433/1, 140; 119/833

(56) References Cited

U.S. PATENT DOCUMENTS 1,130,346 * 3/1915 Swales ................................ 600/243
4,450,831 * 5/1984 Jeffrey .

* cited by examiner

Primary Examiner—Jeffrey A. Smith

(57) ABSTRACT

A speculum (200) for large animals (100) includes an elongated member (20) that extends into the animal's mouth and terminates in a pliable mouthpiece (18) that rests between the animal's molars (110) and (120), or (130) and (140). An outer portion (20) that extends alongside the animal's cheek terminates in a handle (30) which may be held by hand or attached to a halter (52).

7 Claims, 4 Drawing Sheets

Figure 3:
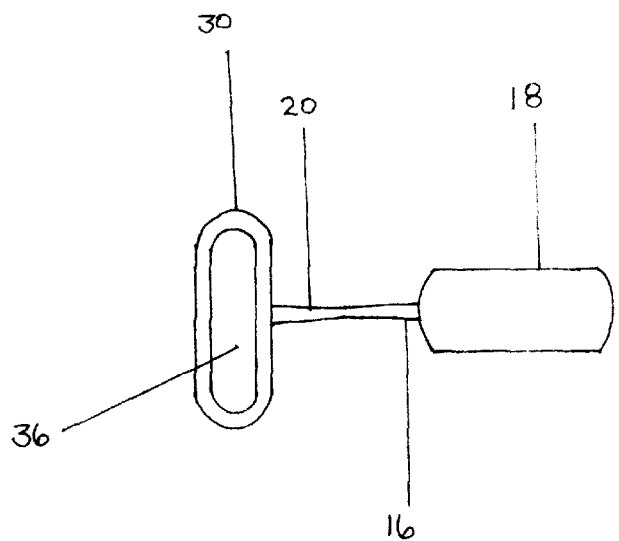

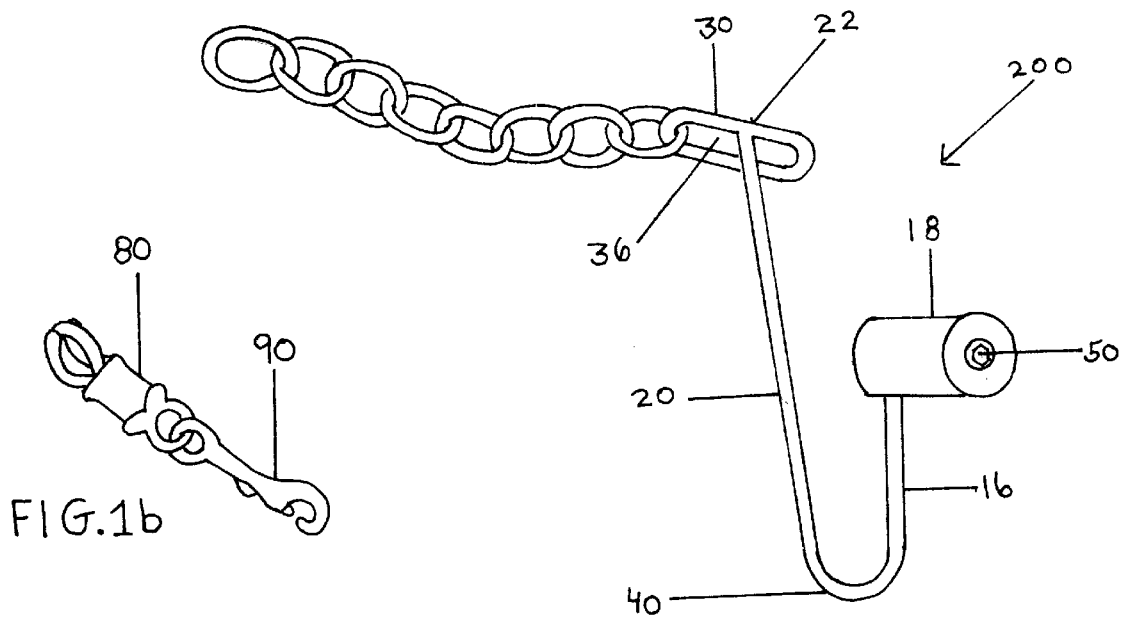
FIG. 1
FIG. 1b
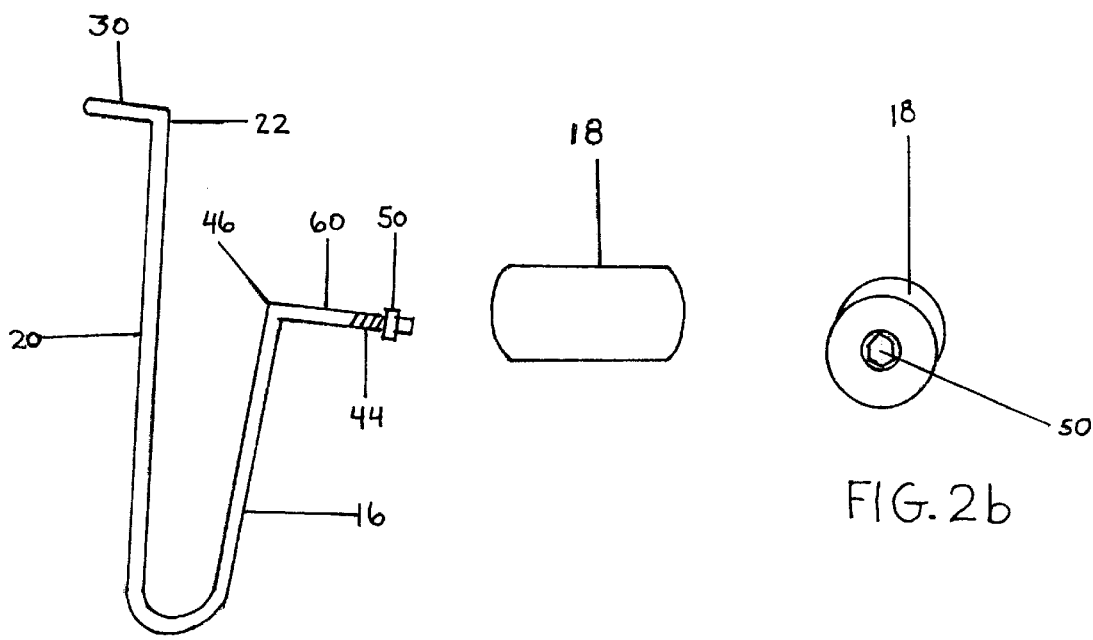
FIG. 2
FIG. 2b

PLIABLE MOUTHPIECE LARGE ANIMAL SPECULUM

CROSS REFERENCE TO RELATED APPLICATIONS

Not applicable

BACKGROUND

1. Field of Invention

This invention is a large animal dentistry tool to provide access to the animal's teeth

2. Description of Prior Art

Horses teeth edges will sharpen in the lateral grinding process of eating. These sharp edges need to be filed smooth or the animal may abrade the soft tissue of its mouth with these sharp edges.

People have in the past inserted solid objects between the animals molars preventing the animal from closing its mouth and providing access to the opposing molars as in U.S. Pat. No. 1,130,346, Frank Swales 1914.

The problem with solid objects is that the animal will chew on the object in its worry of the situation. This can strain the animals jaw muscles as well as crack or chip its teeth.

In U.S. Pat. No. 4,450,831 Louis D. Jeffery 1982 we have the problem of the solid mouthpiece and the additional problem of difficulty removing the speculum if the animal should panic which is not uncommon.

People have also tried other methods to hold open the mouth as in U.S. Pat. No. 5,704,901 Jack Meister 1996, U.S. Pat. No. 442,180 James Halfpenny 1890, U.S. Pat. No. 5,718,665 Clay Stubbs 1997 and U.S. Pat. No. 477,838 Charles Elliot 1892. In each of these devices the tool operates on the animals incisor teeth, holding the jaw very forcefully open with no give or take. Horses being by nature, claustrophobic, can be terrified by this rigid confinement and are subject to panic in this situation. Then there is the difficulty of trying to remove the tool and control a 1,000 lb panicking animal.

SUMMARY

In accordance with the present invention a large animal speculum comprising of a rod-like body with an arcuate end continuing to and terminating in a pliable mouth-piece.

OBJECTS AND ADVANTAGES

Accordingly several objects and advantages of my speculum are: The mouthpiece being pliable will not damage the jaw muscles or chip the teeth. The animal is less likely to panic as it understands there is something in its mouth. The mouthpiece being pliable is less confining to the animal If the animal should panic the tool is very easy to remove. The added benefit being that the animal entertains and distracts itself by chewing on the mouthpiece while this unpleasant but necessary job is performed.

(a) the speculum is easy to get the animal to accept as the mouthpiece being pliable is gentle. Solid mouthpieces are uncomfortable and disquieting to the animal.

(b) the pliable mouthpiece creates a distraction for the animal as the animal will chew on the mouthpiece and relieve stress. Previous speculums afford no distraction (c) removing the speculum is extremely easy as it is provided with a quick release snap. Previous speculums have been hard to remove.

(d) the animal cannot chip or crack its teeth as with solid mouthpieces (e) the animal cannot damage its jaw muscles.

(f) the mouthpiece is replaceable as it wears.

(g) this speculum is an excellent trailing tool for young animals unaccustomed to having their mouth held open.

(h) the mouthpiece can be replaced with varying sizes and shapes to accommodate ponies or foals.

(i) the animal understands why it cannot close its mouth making panicking less likely.

(j) the mouthpiece can be different widths as to how far open the mouth need be.

(k) the body is corrosion resistant.

(l) the handle is oval for ease in grasping and eliminating any sharp edges that could harm human or (m) the mouthpiece can be flavored to add distraction for the animal.

(n) the body can be made in various sizes to accommodate different size animals.

Further objects and advantages are to provide a means to hold open an animal's mouth in a gentle fashion so as to avoid any damage to the animal itself if the animal should panic the tool can easily be removed. Also providing a distraction and stress release for the animal in the form of chewing. Still further objects and advantages will become apparent from a consideration of the ensuing description and drawings.

DRAWING FIGURES

FIG. 1 speculum with mouthpiece attached to inner bite support.

FIG. 1b snap and safety release attached.

FIG. 2 showing inner bite support, threads and nut. Mouthpiece removed.

FIG. 2b mouthpiece with nut in place.

FIG. 3 inverted perspective showing oval handle.

Figure 4:
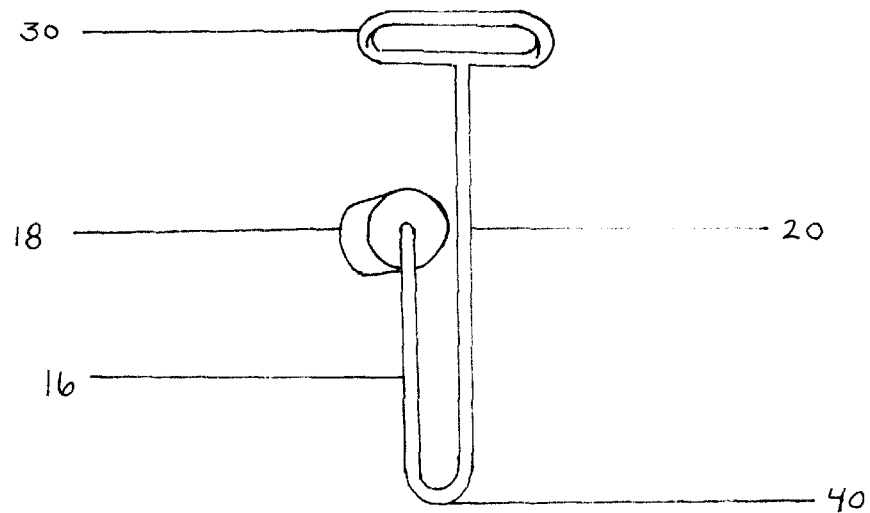

FIG. 4 showing conjunction of body and mouthpiece.

Figure 5:
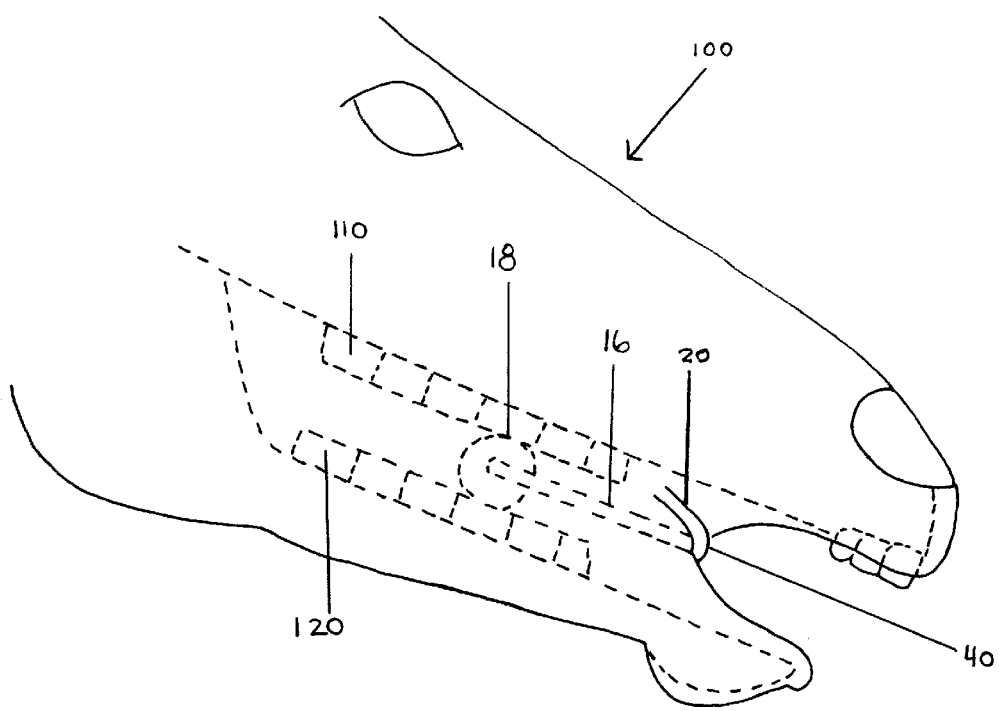

FIG. 5 showing placement of mouthpiece between animals molars.

Figure 6:
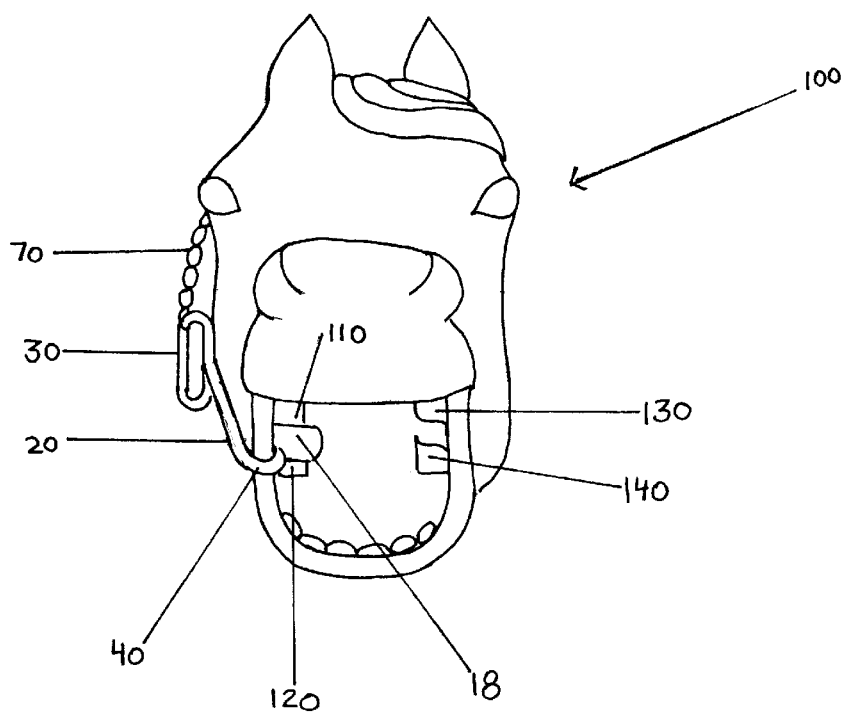

FIG. 6 open mouth view showing accessibility to molars created by speculum.

Figure 7:
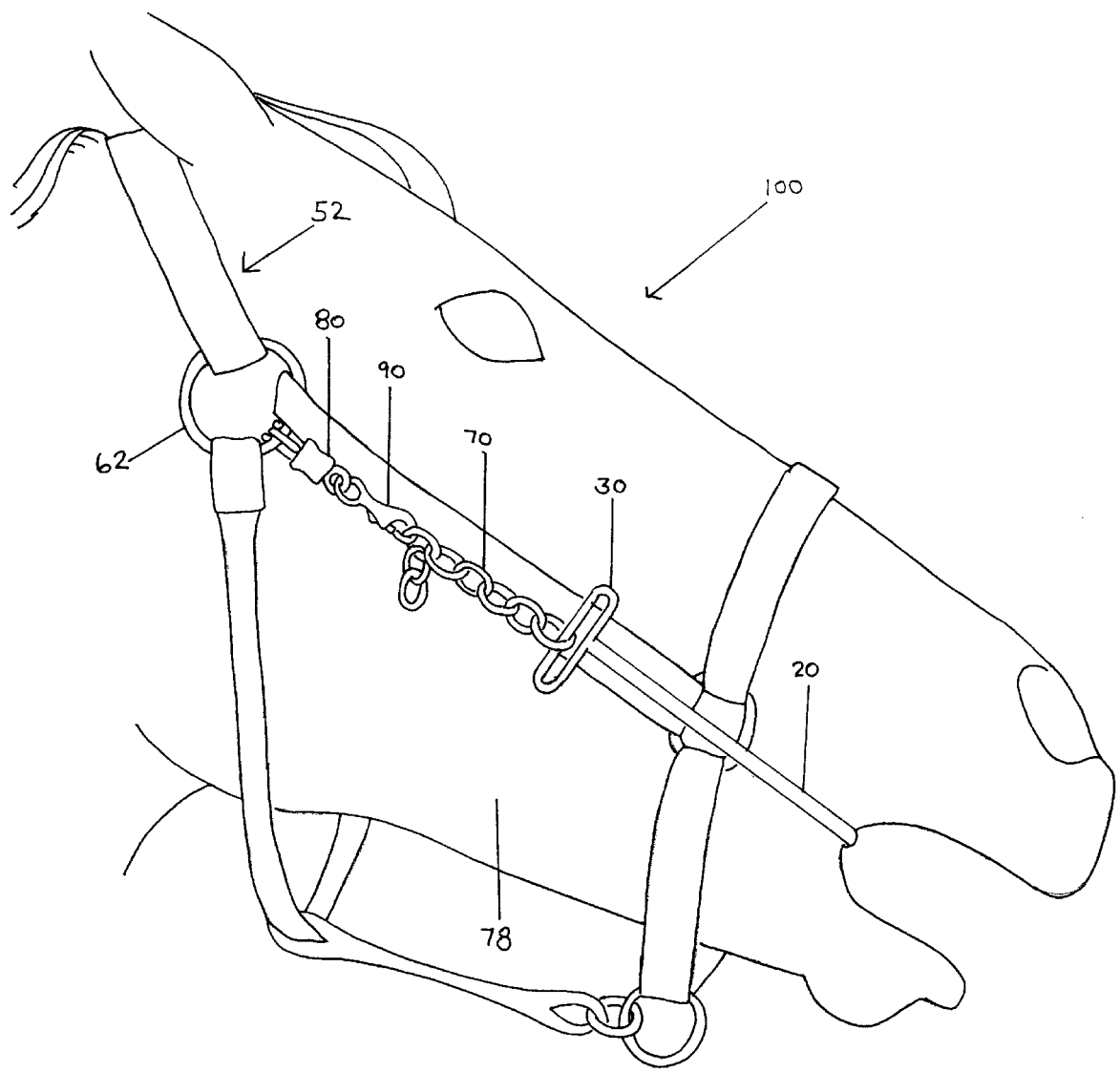

FIG. 7 showing proper way to attach speculum to halter.

| REFERENCE NUMERALS IN DRAWINGS | |
|---|---|
| 16 inner support member | 50 nut |
| 18 mouthpiece | 52 halter |
| 20 body | 60 inner bite support |
| 22 first end | 62 halter ring |
| 30 handle | 70 chain |
| 36 oval | 78 jaw |
| 40 arcuate end SAL 1-9 2000 | 80 safety release |
| 44 threads | 90 snap |
| 46 angle | 100 animal |
| 200 speculum | 110, 120, 130, 140 molars. |

DESCRIPTION

Referring to FIG. 1 an illustration of the top perspective of speculum 200. Showing a body 20 having a fist end 22 and leading to an arcuate end 40. A handle 30 is connected to the first end 22. The handle 30 is formed into an oval 36 attached to the handle 30 is a chain 70. A snap 90 is attached to a safety release snap 80. Arcuate end 40 continues to inner support member 16. FIG. 2 shows the inner support member 16 coming to an angle 46 becoming inner bite support 60. The inner bite support 60 is supplied with the threads 44 to accommodate a nut 50. Also pictured is a mouthpiece 18 at side elevation and the mouthpiece 18 inverted perspective showing the nut 50. FIG. 5 shows placement of the mouthpiece 18 between molars 110 and 120 of a horse 100. FIG. 6 shows the mouthpiece 18, between the set of molars 110 and 120, separating the set of opposite molars 130 and 140. FIG. 7 shows proper attachment of speculum 200 to a halter ring 62 by way of the chain 70 and the snap 90 and the safety release snap 80.

Operation

The horse 100 is first fitted with the halter 52 to accommodate the jaw 78 as it opens. The safety snap 80 is attached to the snap 90 and is then attached to halter ring 62. Attendant grasps the handle 30 and guides the mouthpiece 18 between the horses 100 set of molars 110 and 120 or 130 and 140 holding the snap 90 attendant then will affix the snap 90 to the chain 70 where it is most comfortable for the horse 100. To remove speculum 200 from horse 100 unsnap the snap 90 from the chain 70 and grasp the handle 30 and ease the mouthpiece 18 out of mouth. In emergency pull down on the safety snap 80 and speculum 200 will be released from the horse 100 and the halter 52. To remove and replace the mouthpiece 18 unscrew the nut 50, slide mouthpiece off the inner bite support 60 and put the new mouthpiece 18 on. Screw the nut 50 back on the threads 44.

Conclusion, Ramification and Scope of Invention

Thus the reader will see that the speculum I have invented will provide a gentle means to hold open a horses mouth, reducing the risk of panic in the horse and giving the horse a way to distract itself while it's teeth are worked on. Also providing a quick release method in the case of an emergency.

While my above description contains some specificities, these should not be construed as limitations on the scope of the invention, but rather as an exemplification of one preferred embodiment thereof. Many other variations are possible for example: the mouthpiece can be in many different sizes, shape or various levels of pliability. The whole speculum can be made in one piece, and the mouthpiece may also be treated with a smell or taste to make it even more acceptable to the animal. The body of the speculum may be in different lengths and sizes to fit different sized animals. The means of attachment to the halter can also be of different materials and methods i.e. tying with a rope. Accordingly, the scope of the invention should be determined not by the embodiment illustrated but by the appended claims and their legal equivalents.

What is claimed is:

1. A speculum for holding open a large animal's mouth, said speculum comprising:
    a) a body having a first end attached to a handle and an arcuate end which continues to an inner support member placeable within said animal's mouth, the inner support member being attached to an inner bite support; and
    b) a pliable mouthpiece removably attached to said inner bite support;
    wherein said mouthpiece is placeable between opposing upper and lower teeth of said animal to hold said animal's mouth open.

2. A speculum as recited in claim 1, and further comprising:
    c) means for attaching said body to a halter.

3. A speculum as recited in claim 1, wherein said attaching means comprises a chain or a rope.

4. A speculum as recited in claim 3, wherein said attaching means further comprises a first snap and a safety release snap, said first snap is removably attachable to said chain or rope, and said safety release snap is attached to said first snap and is releasably attachable to said halter.

5. A speculum as recited in claim 2, wherein said attaching means comprises a first snap attached to a safety release snap.

6. A speculum as recited in claim 1, wherein said mouthpiece is removably attached to said inner bite support to facilitate the interchange of a selected mouthpiece having a particular characteristic, said characteristic being selected from the group consisting of size, shape, smell, taste, levels of pliability, condition and combinations thereof.

7. A speculum as recited in claim 1, wherein said inner bite support is supplied with threads, and wherein said speculum further comprises a nut removably connected to said inner bite support via said threads.

* * * * *